United States Patent
Kadouche et al.

(10) Patent No.: US 7,153,506 B2
(45) Date of Patent: Dec. 26, 2006

(54) USE OF ANTI-FERRITIN MONOCLONAL ANTIBODIES IN THE TREATMENT OF SOME CANCERS

(75) Inventors: Jean Kadouche, Paris (FR); Rafael Levy, Montrouge (FR)

(73) Assignee: Monoclonal Antibodies Therapeutics "M.A.T.", Paris (FR)

( * ) Notice: Subject to any disclaimer, the term of this patent is extended or adjusted under 35 U.S.C. 154(b) by 353 days.

(21) Appl. No.: 09/952,307

(22) Filed: Sep. 13, 2001

(65) Prior Publication Data

US 2002/0106324 A1    Aug. 8, 2002

Related U.S. Application Data

(63) Continuation of application No. PCT/FR01/00192, filed on Jan. 19, 2001.

(30) Foreign Application Priority Data

Jan. 20, 2000    (FR) ................... 00 00718

(51) Int. Cl.
*A61K 39/395* (2006.01)
(52) U.S. Cl. ............... 424/141.1; 424/134.1; 424/138.1; 424/9.34
(58) Field of Classification Search ............... 424/9.34, 424/141.1
See application file for complete search history.

(56) References Cited

U.S. PATENT DOCUMENTS 5,156,840 A * 10/1992 Goers et al. ................ 540/145
5,538,726 A     7/1996 Order
5,843,440 A    12/1998 Pouletty et al.

OTHER PUBLICATIONS

"Isotopes" downloaded from the url . . . www.fact-index.com on Nov. 2, 2004.*
Vriesendorp et al., (Journal of Clinical Oncology, vol. 9, pp. 918-928).*
Houghton et al., (Jul. 1983, J. Exp. Med., vol. 158, pp. 53-65).*
Ono et al., "Common epitopes in human isoferritins characterized by murine monoclonal antibodies," *J. Biochem.*, 99: 269-279 (1986).
Hahn et al., "Basic and acidic isoferritins in the sera of patients with neuroblastoma," *Cancer*, 62: 1179-1182 (1988).
Kadouche et al., "Analysis of varios isoferritins with monoclonal antibodies," *Iron Building Proteins*, 295: 187-190 (1982).
Boerner, P. et al., "Production of Antigen-Specific Human Monoclonal Antibodies From in Vitro-Primed Human Splenocytes", *The Journal of Immunology*, 147:86-95 (1991).
Brams, P. et al., "Antigen-Specific IgG Responses from Naïve Human Splenocytes: In Vitro Priming Followed by Antigen Boost in the Scid Mouse", *The Journal of Immunology*, 160:2051-2058 (1998).
Order, St. et al., "A New Method for Delivering Radioactive Cytotoxic Agents in Solid Cancers", *Int. J. Radiation Oncology Biol. Phys.*, 30(3):715-720 (1994).
"Serine Esterase: Enzyme which catalyzes the hydrolysis of esters and is characterized by a catalytically active serine residue in its active site", Search of Swiss Prot database using keyword: Serine Esterase, http://www.expasy.org/cgi-bin/get-entries?KW=Serine%20esterase and http://www.ca.expasy.org/cgi-bin/sprot-search-de?serine%20esterase, search printed after Mar. 29, 2005.
"Serine Protease: Proteases, proteinases or peptidases describe the same group of enzymes that catalyse the hydrolysis of covalent peptidic bonds. In the case of serine proteases the mechanism (from Mellon College of Science Courses) is based on nucleophilic attack of the targeted peptidic bond by a serine", http:www.biochem.wustl.edu/~protease/ser_pro_overview.html and http://www.biochem.wustl.edu/~protease/ser_pro_seq_list.html, printed Apr. 4, 2005.
Jeanteur, P., c-Myce an iron oncogene, *Bulletin du Cancer*, 86:250 (1999) (english translation).
Friguet et al., "Measurements of the True Affinity Constant in Solution of Antigen-Antibody Complexes by Enzyme-Linked Immunosorbent Assay", *Journal of Immunological Methods*, 77 (1985) 305-319.

\* cited by examiner

*Primary Examiner*—Misook Yu
(74) *Attorney, Agent, or Firm*—Merchant & Gould P.C.

(57) ABSTRACT

The invention concerns the use, in the preparation of a medicine for treating cancer whereof the cells exhibit overexpression of a product of a gene of the myc-related family, of an anti-ferritin monoclonal antibody or a fragment thereof, said antibody or said fragment identifying an epitope common to acidic and basic human ferritins.

19 Claims, 3 Drawing Sheets

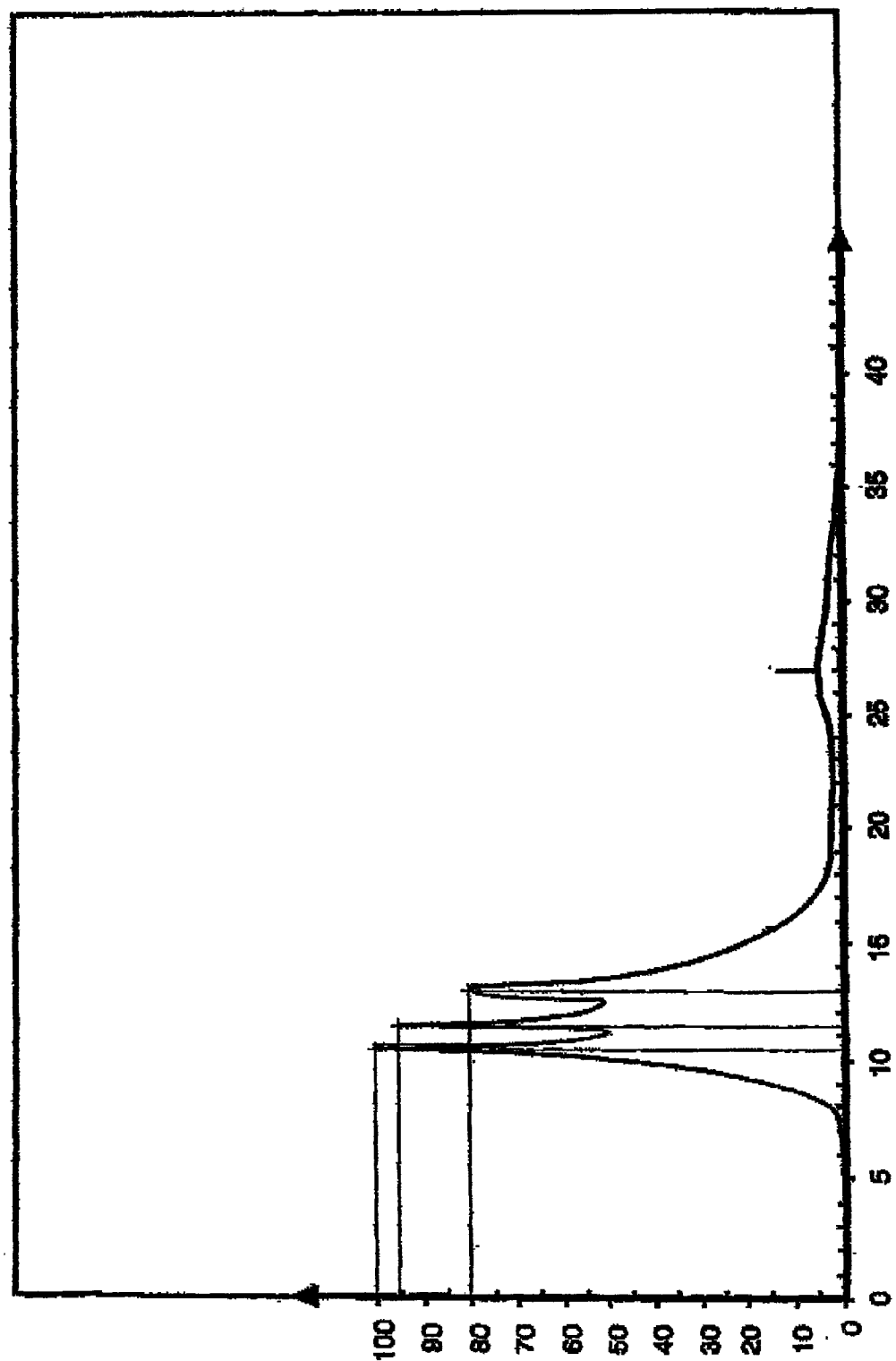

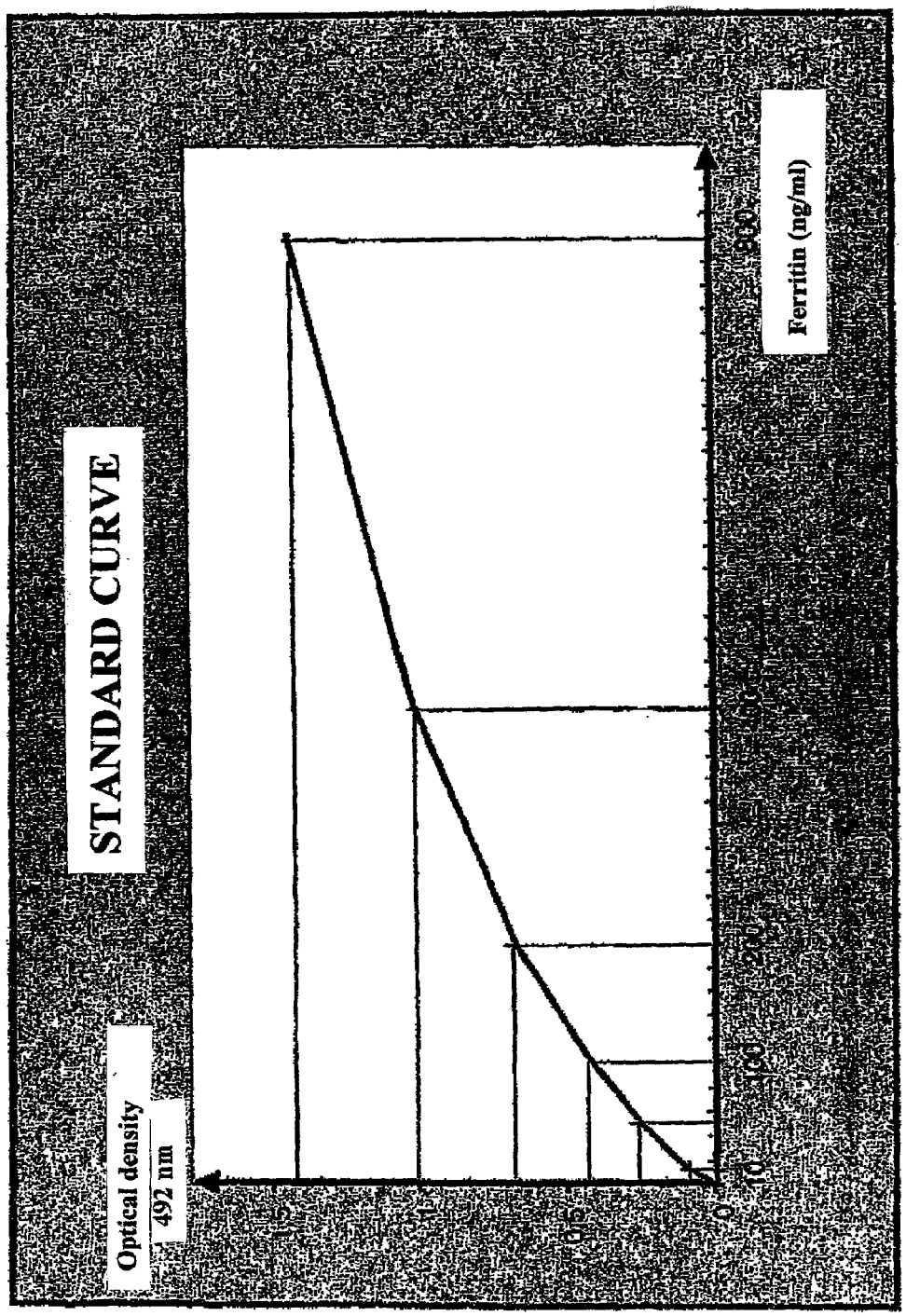

USE OF ANTI-FERRITIN MONOCLONAL ANTIBODIES IN THE TREATMENT OF SOME CANCERS

CROSS REFERENCE TO RELATED APPLICATION

The present application is a continuation under 37 C.F.R. § 1.53 (b) and 35 U.S.C. § 111 (a) of pending prior international application number PCT/FR01/00192, filed on Jan. 19, 2001.

BACKGROUND OF THE INVENTION

1. Field of the Invention

The present invention relates to the provision of novel means for the diagnosis and therapy of cancers characterized by overexpression of gene products from the myc family. These means essentially include the use of monoclonal antibodies recognising an epitope common to acidic and basic isoferritins.

2. Description of the Related Art

Ferritin is a protein with a molecular weight of 440000 kDa used to store iron in cells. Since 1942, the date at which GRANICK isolated hepatic ferritin and until recently, this molecule was considered to be a uniquely cellular iron storage protein mainly located in the liver, the spleen and the bone marrow. It only appears in the serum in the event of a substantial overload of iron or during hepatic necrosis with liberation of this tissue protein into the vascular space. More sensitive detection methods using radioactive, enzymatic or fluorescent tracers have demonstrated the existence of a base concentration of serum ferritin and have allowed the study of variations thereof during the course of various diseases. At the same time, a number of research teams have endeavoured:

- to refine knowledge regarding the biochemical structure of tissue ferritin;
- to discover the reasons for the heterogeneity of the molecular forms grouped under the term "isoferritins";
- to compare the different characteristics of ferritin extracted from plasma or from different healthy or diseased organs.

Current data show that ferritin is a macromolecular structure constituted by a glycoprotein structure in the form of a shell, Apoferritin, which is the protein component and which encloses a metallic core of iron atoms distributed in iron crystals inside its cavity.

X ray crystallographic analysis of ferritin has shown the presence of 24 sub-units, distributed in a rigorous symmetry. The sub-units are of two types, H and L.

The genes coding for each of the sub-units have been cloned and their chromosomal location is known (Murow H. N., Aziz N., Leibold E. A. et al., The ferritin gene's expression and regulation, Ann. NY Acad. Sci. 1988, 528 113). The H type sub unit, with a molecular weight of 21 000, is in the majority among the most acidic isoferritins such as ferritin extracted from HeLa cells or ferritin of cardiac origin (H=heart), but it is also present to a lesser extent in the liver and spleen. The second type of sub-unit (L), with a molecular weight of 16000, is more specifically in the majority in the most basic molecules of hepatic origin (L=liver) or originating in the spleen.

The iron stored in ferritin is mobilised for the synthesis of proteins that incorporate ferrous or ferric ions as functional components (haemoglobins and enzymes such as cytochromes and catalases). The principal functions of ferritin in the liver, spleen and marrow are firstly to protect tissues from oxidation and damage caused by free radicals produced by interactions with iron, water and oxygen, and secondly to re-use iron for the synthesis of haemoglobins. In other organs or in plasma, ferritin contains little or no iron and its function is poorly understood.

It has long been known that different ferritin phenotypes exist (isoferritins) (Drysdale J. W. (1977), Structure and metabolism, (Ciba Foundation Symposium 51, New Series), pages 41–57. In 1965, Richter demonstrated that ferritin prepared from human liver and carcinomatous epidermoid HeLa cells had different electrophoretic migration rates, that could not be explained by differences in the iron content. In total, about twenty isoferritins were characterized.

Techniques such as electrofocussing, ion exchange chromatography and two-dimensional electrophoresis under denaturing conditions showed that isoferritins are formed by variable combinations of the two sub-units H and L (Murow et al., supra).

The role of basic isoferritins is well known, particularly that of serum ferritin in phenomena directly linked to iron metabolism. That of acidic ferritins is controversial: many authors have used it as a tumoral marker in man. In 1968, a α2H globulin, later termed α2H isoferritins was discovered in serum from patients with different neoplasias (Buffe D. et al., Presence d'une protéine d'origine tissulaire α2-Hglobuline dans le serum de sujets atteints d'affections malignes [Presence of a protein originating from tissue α2H globulin in the serum of subjects with malignant disorders], Int. J. Cancer (1968) 3: 850–856). Marcus D et al., (J. Natl. Cancer Disti. (1975) 55: 791–795) described an abnormal ferritin in the serum from patients with breast cancer. Drysdale J. et al., (Cancer Res. (1974) 34: 3352–3361) described an acid isoferritin identical to the ferritin contained in HeLa cells with a particularly high concentration in different types of neoplasia. Moroz C. et al., (Clinical Exp. Immunol. (1977) 29: 30–76) describe a factor, which is an isoferritin, secreted by a sub-population of T lymphocytes present in particular in breast cancer and Hodgkin's disease. Finally, it should be noted that the majority of human neoplastic processes (Hodgkin's disease, breast, ovarian, pancreas, lung cancers, epidermoidal cancers of the head and neck, neuroblastoma, acute lymphoblastic leukaemia (ALL), Kaposi sarcomas, etc. . .) are accompanied by an elevation in serum ferritin. In all cases, a high level of serum ferritin is a negative prognostic factor (Hann H. W., Evans A. E., Siegel S. E. et al., Cancer Res., (1985) 45; 2843–2848; Jacobs A., Slater A., Wittaker J. A. et al., J. Cancer, (1976) 34: 533).

It has also been shown that in several types of cancer, there is a local tumoral increase in tissue ferritin, although the stromal or purely tumoral reactional origin of this excess ferritin has not been formally defined. Nevertheless, all authors are in agreement that it concerns acidic ferritin.

The development of antibodies and in particular monoclonal antibodies in imaging or for the treatment of certain diseases has been the aim of many developments.

A review of these developments was published in 1998 (P. S. Multani et al., (1998), Journal of Clinical Oncology, vol. 11. 16: 3691–3710). The diagnostic or therapeutic use of antibodies in a cell screening system with substances with a selective toxicity to specifically eliminate pathological cells is known as the magic bullet.

Briefly, the different possibilities for using monoclonal antibodies in this context are as follows:

a) the use of native antibodies as an immune effector, used in anti-tumoral therapies with a CDCC (complement-dependent cell cytotoxicity) activity or an ADCC (antibody-dependent cell cytotoxicity) activity. The antibody with a certain specificity as regards this target cell via its Fab fragments can then cause a cellular immune reaction due to Fc fragments of the same antibody. It can also involve blocking a receptor of the target cell or an anti-idiotypic vaccination specific for the tumoral antigen;

b) the antibody can be coupled to a toxin or a drug; the antibody is then a vector that transports said toxin or drug to the target;

c) antibodies can also act as a galenical vector by coupling with liposomes or other analogous systems into which cytoxic substances or drugs or anti-sense oligonucleotides, etc . . . can be introduced.

d) the antibodies can be directly or indirectly radiolabelled (chelate or bispecific antibody with an "antichelate, etc" site) and their radiation can be used for therapeutic ends or for imaging. A number of possible isotopes exist, in particular for labelling the antibodies. The most frequently used isotope is iodine 131. This method has a number of disadvantages (iodine fixing in the thyroid, existence of endogenous dehalogenases). Further, iodine 131 does not emit pure β radiation. Finally, its range length is short (1.1 mm).

Coupling to indium 111 for imaging or yttrium 90 for therapy has also been developed. In that case, coupling is generally carried out by grafting a chelate to an antibody, the chelate fixing the radioactive emitter using techniques described and developed by the team headed by S. M. Quadri and H. M Vriesendorp (Vriesendorp H. M. et al., (1991), J. Clin. Oncol. 9: 918–928; P. E. Borchardt et al., (1998), The Journal of Nuclear Medicine 39: 476–484). The choice of yttrium 90 as a therapeutic radio-isotope is pertinent to cancerology. That isotope emits a pure β radiation; its half-life is 67 hours and its range length is 6.6 mm. It appears to be well adapted to treating solid tumoral masses, in particular Hodgkin's disease and malign non Hodgkin's lymphomas. Encouraging results have been obtained by the same team (H. M. Vriesendorp et al., (1995), Cancer Research 55, 58–92). These authors describe trials with polyclonal antiferritin antibodies labelled with Y 90 in patients with Hodgkin's disease resistant to conventional treatment methods combining chemotherapy and external radiotherapy and bone marrow grafts.

One of the biological characteristics of this disease is hyperexpression of ferritins by tumoral cells and the reactional cells surrounding them. Imaging tumour sites (indium 111) and the treatment of resistant forms of this disease by the system described in Vriesendorp et al., (1995), Cancer Research 55: 58–92 has produced good results.

Further, it is known that the myc oncogene family (the most important are c, N. L) codes for nuclear proteins that bind to DNA. In a normal cell, transcription of myc genes increases in the hours following a mitogenic signal. Proteins coded by the genes from the myc family have a "leucine zipper" moiety. This structure enables the formation of heterodimers (with c-fos or c-jun) or homodimers. Currently, the function of the c-myc product is viewed as being that of regulation of the transcription of cellular genes involved in mitosis initiation. In summary, myc genes acquire oncogenic properties by mechanisms that result in an overexpression of their products. This overexpression can be a result of:

gene amplification; or
activation of gene transcription; or
post-transcriptional modifications involving increased stability of mRNA. In vivo studies on the overexpression of the products of genes from the myc family in different tissues by the creation of transgenic animals has confirmed these facts. Finally, any increase in proliferation is physiologically accompanied by an increased expression of genes from the myc family.

The three principal members of the myc family (c, N, L) are among the most frequently found oncogenes in human cancers that are activated by these three different mechanisms. In particular, c-myc is found in malignant lymphomas, L-myc and N-myc in small cell lung cancers and neuroblastomas from which the latter has been characterized. In the majority of malign human tumours, the degree of expression of myc genes is a negative prognostic factor.

Known target genes for which transcription is regulated by the products of genes from the myc family are few. The gene coding for the H chain of ferritin is the latest gene for which it has just been shown that it is negatively regulated by the product of the c-myc gene (Wu et al., Coordinated regulation of iron controlling genes, H ferritin and IRP2 c-myc, Science (1999) 283: 676–679). In other words, expression of the c-myc gene and/or other members of this family in cancer cells is inversely proportional to ferritin expression.

SUMMARY OF THE INVENTION

The present invention results from the unexpected and unenvisaged observation from the available information discussed above whereby after immunising mice with a ferritin extracted and purified from a human spleen, certain monoclonal antibodies had a very high specificity in targeting cancer cells or cancers in which the myc gene is overexpressed.

BRIEF DESCRIPTION OF THE DRAWINGS

FIG. 2 represents a chromatogram obtained after purification on a Superdex 200-26/60 column using the purification technique as described in Table II.

FIG. 3 is a curve showing the results of a sandwich ELISA test using AMB 8LK as the solid phase and AMB 8LK labeled with alkaline phosphatase in human serum.

DETAILED DESCRIPTION OF THE PREFERRED EMBODIMENTS

Figure 1:
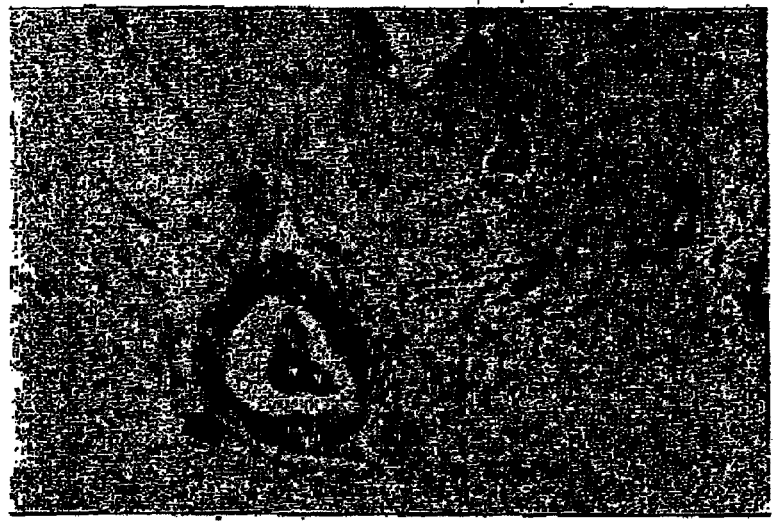
Fig 1A is a photograph of a histochemical section of ganglions from Hodgkin's disease labeled with AMB 8LK and treated as described in Example 1.
FIG. 1B is a photograph of a histochemical section of ganglions from Hodgkin's disease labeled with AMB 8LK and treated as described in Example 1.
FIG. 1C is a histochemical section of pancreatic adenocarcinoma labeled with AMB 8LK and treated as described in Example 1.
Figure 1:
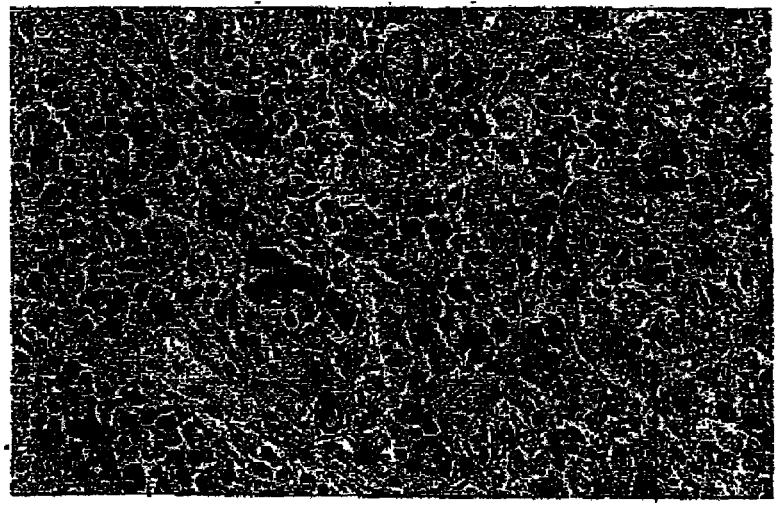
Figure 1:
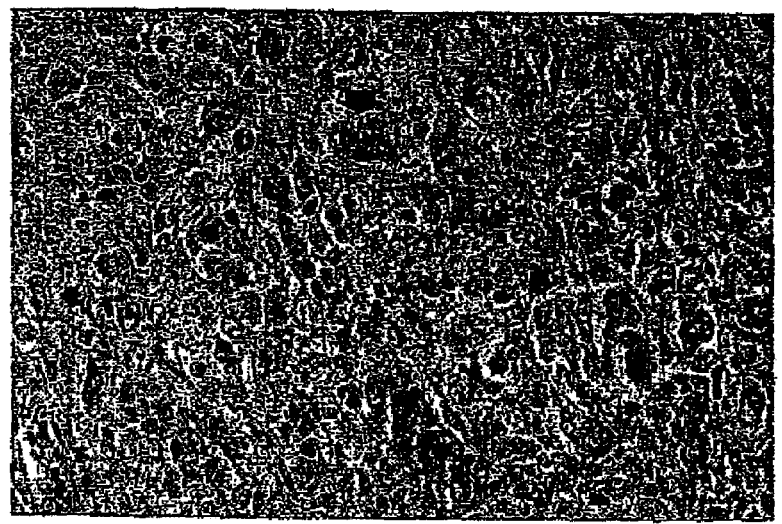

The ferritin extraction-purification technique used can obtain two, acidic and basic, forms of ferritin with a high degree of purity. The extraction-purification technique used in the present invention particularly consists of extracting and purifying human ferritins extracted and purified from patients with microcytic anaemia. Unexpectedly, certain monoclonal antibodies, obtained using the conventional Köhler and Milstein technique, recognise an epitope common to all acidic and basic, uniquely human isoferritins (J. Kadouche et al., C. R. Acad. Sc. Paris (1982) t. 295 series III, page 443). Monoclonal antibodies are screened in two steps: i) selection of antiferritin antibodies by capture on a solid base coated with the same ferritin as that used to immunise animals; ii) revealing and fixing specific antiferritin antibodies fixed to this solid phase by adding the same ferritin, radiolabelled with iodine 125, to the wells. Selection of antibodies on a solid phase using purified ferritin and using iodine-125 labelled ferritin can select antibodies directed against a common and repetitive epitope in all human acidic and basic isoferritins. The term "repetitive epitope" means that the same epitope is present a number of times in the molecule.

The invention also results from a demonstration whereby, in contrast to that which could be predicted from the article by Wu et al., (supra), specific monoclonal antibodies for the two forms of ferritin recognise tumour cells or cancerous cells in which the C-myc gene is overexpressed.

The present invention concerns the use, in the production of a drug for cancer therapy in which cells overexpress the product of a gene from the myc family, of an antiferritin monoclonal antibody or a fragment thereof or a construction including such a fragment, said antibody or said fragment recognising an epitope that is common to acidic and basic human ferritins.

The term "construction including a fragment of antibody" means a product of a polynucleotide sequence coding said fragment and a polypeptide with a stabilising or transport function, such as albumin, ovalbumin or a fragment thereof. It can also mean a conjugate combining the antibody or antibody fragment with an adjuvant and/or a molecule or structure ensuring transport and/or stability of said antibody, such as liposomes, cationic vesicles or nanoparticles. Finally, it can mean a combination of the product of a sequence as described above conjugated with an adjuvant and/or a molecule or structure ensuring transport and/or stabilisation of the molecule.

Therapeutic or diagnostic use in vivo of monoclonal antibodies requires that they combine particular qualities of specificity, affinity and non-toxicity. The term "non-toxicity" means the fact that they do not cause immune reactions or rejections in relation to a substance that can be administered long-term and in any event repeatedly. The term "specificity" means the fact that the monoclonal antibodies in question do not cross-react with antigens other than ferritins.

In terms of specificity, it is important that the antibody recognises both acidic isoferritins (specific for neoplastic processes, H form) and basic isoferritins (martial metabolism, L form).

The antiferritin monoclonal antibody of the invention must also have an affinity for the corresponding antigen that is sufficient to eliminate the diffusion of this antibody as much as possible, if necessary carrying a toxic or therapeutic substance into healthy tissue or cells. In the present invention, the affinity for ferritins must be more than $10^{-9}$ mole/litre.

Further, the epitope that is common to acidic and basic isoferritins is preferably a repetitive epitope. Repetition of the same epitope on the isoferritins allows a number of antibodies to fix to the same molecule of ferritin. The diagnostic and therapeutic properties of the resulting coupling products from these antibodies are advantageously improved in this manner.

The invention also concerns antiferritin monoclonal antibodies for diagnosis or therapy of cancers or tumour cells in which overexpression of a gene from the myc family is observed and which has the following characteristics:

it recognises an epitope that is common to acidic and basic ferritins and, preferably, it does not recognise non human ferritins; more preferably, said epitope that is common to acidic and basic ferritins is a repetitive epitope;

its affinity for the antigen is more than $10^{-9}$ mole/litre.

The antibodies of the invention are preferably kappa type IgG immunoglobulins. However, they can also be IgM immunoglobulins which, because they have a plurality of epitopic recognition sites, can improve targeting. When an injection is made directly into the lesion in vivo, IgM is preferred in that it has ten antigen binding sites: the yield is thus higher.

The term "diagnosis" means both in vitro immunoscintigraphic diagnosis and any in vivo diagnostic method using monoclonal antibodies as a vector for a substance allowing its localisation.

The quality of the monoclonal antibodies used in the invention results firstly from the quality of the antigen used for immunisation and secondly, from its degree of purity.

The ferritin used to immunise mice in the process for obtaining monoclonal antibodies originates from a pathological spleen from a patient with Minkowski-Chauffard's syndrome extracted using the modified Granick method using ammonium sulphate and cadmium sulphate. This extracted and purified ferritin was used in the protocol described in Example 1 below to immunise mice to obtain hybridomas producing monoclonal antibodies.

Table I below summarises some of the characteristics of the antibodies obtained after cloning the hybridomas obtained using the purification, extraction and immunisation technique of the invention.

This table indicates the denomination of the monoclonal and polyclonal antibodies tested, their isotypic nature, their affinity for ferritins and the reactivity to a whole series of ferritins measured by precipitation using Ouchterlony's immuno-diffusion technique. The antibodies used in the invention must have a negative reactivity for all non human cells or tissues, namely horse spleen and LIA (lemia inhibitor activities), which is not the case for any of the polyclonal antibodies, nor for M211 monoclonal antibody.

A further characteristic of the antibodies used in the invention is their affinity constant; it appears that among the antibodies in this table, only B8 and M29 can be used in the invention.

Finally, in a particular implementation, the antibodies of the invention are directed against a repetitive epitope common to acidic and basic isoferritins. Such antibodies are demonstrated by a sandwich ELISA test as described in Example 2 below and illustrated in FIG. 3. Being able to carry out such a test confirms that a plurality of antibodies can fix to the same ferritin molecule. This property endows it with a definite advantage as regards their diagnostic or therapeutic use.

| Monoclonal antibody | M 29 | M 211 | M 386 | B 8 | — | — | — |
|---|---|---|---|---|---|---|---|
| Polyclonal antibody | — | — | — | — | F1 | F2 | F3 |
| Isotypes | Ig G1K | Ig G1K | Ig G2b K | Ig G1 K | — | — | — |

-continued

| | | | | | | | |
|---|---|---|---|---|---|---|---|
| Affinity constant (I/mol) | $2.3\ 10^{-10}$ | $1.3\ 10^{-8}$ | $2.2\ 10^{-8}$ | $5.1\ 10^{-9}$ | $1.3\ 10^{-11}$ | $5.9\ 10^{-11}$ | $4.0\ 10^{-11}$ |
| Reactivity: | | | | | | | |
| human liver | + | + | + | + | + | + | + |
| human spleen | + | + | + | + | + | + | + |
| human heart | + | + | + | + | + | + | + |
| human placenta | + | + | + | + | + | + | + |
| HeLa cells | + | + | + | + | + | + | + |
| Horse spleen | − | + | − | − | − | + | + |
| LIA | − | − | − | − | + | + | + |

In vivo use of murine or animal monoclonal antibodies is, however, limited because of the production by the organism of anti-species antibodies rapidly rendering iterative injections ineffective or even dangerous (anaphylaxis, immunocomplex disease, production of anti-idiotypic antibodies). It is thus preferable to eliminate the Fc portions from these murine antibodies either by humanisation or by reconstitution. The solution consisting of developing chimeral antibodies has often been used (Nature 321 (1986) 326: 522–525). It is now possible to clone the genes coding for the two chains of the monoclonal antibodies produced by hybridomas, and these can be manipulated in vitro and then re-introduced into the secreting cells, such as lymphoid lines or the like, after their re-insertion into the selected cells in appropriate expression vectors. New monoclonal antibodies are then constructed with variable regions from mice or rats and human constant regions. Different types of immunoglobulins can be obtained. Their specificity in all cases will be the same as that from the variable regions used, but they will have the effective properties of human immunoglobulins that depend on the isotype selected for construction.

A second approach consists in reshaping the antibodies (Riechmann et al., (1988), Nature 332: 323–327). Briefly, the starting point for this approach is the observation that the contact sites for antibodies with the antigen epitopes they recognise are located on certain sequences of the variable regions termed hypervariable regions. The technique consists in grafting the hypervariable regions of a murine immunoglobulin termed the complementarity determining region (CDR) onto variable regions of a human class G immunoglobulin.

Finally, Clackson et al., (1991), Nature 352: 624–628 and the team headed by Lerner (Huse et al., (1989), Science, 246: 1275–1281) used PCR to amplify V genes of expressed heavy chains of murine G immunoglobulin. Different libraries were then created from the genomic DNA extracted from immunised mouse spleens. A library of vectors carrying variable gene sequences from all of the antibodies was produced. A λ bacteriophage was used as an expression vector in E. coli. This technique produced single chain VH domains of the antibodies. Then, single chain Fv fragments were produced, obtained from a VH region, linked to a VK domain via a linker, using PCR. This method could simply and cheaply produce specific fragments in a non-immunogenic environment.

Finally, the monoclonal antibodies of the invention, whether IgG of IgM, can be monospecific, bi-specific or polyspecific. The genetic manipulation techniques described above can combine specificities firstly for ferritin and secondly, for a receptor or surface antigen specific surface for a cell to be targeted.

A variety of possibilities exist for using monoclonal antibodies in the magic bullet concept. The first is to use antibodies as an immune effector, employed in anti-tumoral therapies with a CDCC (complement-dependent cell cytotoxicity) activity or an ADCC (antibody-dependent cell cytotoxicity) activity. It may also concern blocking a receptor of the tumour cell or an anti-idiotypic vaccination specific for the tumour antigen.

In the use of the invention, the antibody or fragment thereof can be coupled to a molecule X, where X is a toxic molecule, a drug or a prodrug or a nucleotide sequence or a second antibody regardless of its recognition specificity.

a) X is a toxic molecule:

A first example is the case where X is a radioactive isotope, preferably a β emitter. A number of possibilities exist for coupling radioactive isotopes to proteins, in particular monoclonal antibodies. A number of studies using antiferritin polyclonal antibodies labelled with indium 111 (In 111) and yttrium (Y 90) have produced interesting results concerning imaging tumour sites, preferably with In 111, and concerning the treatment of refractory forms of Hodgkin's disease (Y 90) (P. E. Borchardt et al., (1998), The Journal of Nuclear Medicine, 39, n° 3, page 476).

Whether IgM or IgG, the radioactive isotope is coupled to the antibody by the chelation techniques described, namely Borchardt et al., (supra).

The choice of yttrium 90 as therapeutic radioelement is particularly pertinent: it is a pure β emitter with a half-life of 67 hours and a range length of 6.6 mm. It appears to be perfectly suited to treating tumour masses, in particular Hodgkin's disease, lymphomas or cancers of the pancreas.

X can also be a toxic A chain ricin or abrin molecule, or A chain diphtheria toxin. The toxicity of these polypeptides is well known. They can be coupled to immunoglobulin by carboxyl type bonds or by any bond type that can couple proteins together, in particular via their —COOH, —NH$_2$, —SH residues, etc., which are well known to the skilled person.

b) X is a cytotoxic molecule:

Cytotoxic drugs are known, others are being developed. They can block cell division, either by blocking transcription or by blocking translation or by inducing apoptosis. Examples that can be cited are mitomycin, adriamycin, taxol, etc. The problem with using such drugs is their toxicity towards healthy cells or tissue. The monoclonal antibodies of the invention, which are monospecific for ferritin or bi-specific as regards ferritin and a receptor, allow these substances to be targeted to the selected cells.

c) X is a galenic vector or a prodrug.

To improve the stability and avoid biodegradation or toxic activity towards healthy cells, the monoclonal antibody of the invention can be coupled to a liposome type vector or to cationic type emulsions already used as a drug administration system (Texeira et al., (1999), Pharmaceutical Research, 16, 30–46). It can also be a cationic lipid such as those described by D. Deshpande et al., (1998), Pharmaceutical Research, 15: 1340–1347. Integrating cytostatic and/or cytotoxic molecules of the antisense RNA and DNA type into this type of vector is particularly appropriate. However, for the reasons given above and with the aim of increasing the targeting specificity and reducing the cytotoxicity of the different toxins used, the molecules cited in point b) above can advantageously be carried by these vectors.

d) X is a second antibody,
either directed against ferritin allowing cross-linking of several ferritin molecules;
or directed against an antigen for dendritic lymphoid cells, macrophage cells or natural killer cells (such as CD20, CD30, CD33, HNK1, CD56), to recruit said cell and activate it in the tumour cell;
or directed against a receptor located on the target tumour cell to allow cross-linking of the target cell with the ferritin.

In points a), b), c) and d) above, X can also be coupled to a carbon chain sensitive to esterases. This chain, with a length of 5 to 15 carbon atoms, linear or branched, is sensitive to esterases. Coupling the X molecule to this type of chain in therapeutic use is of particular advantage since healthy cells have enzymatic systems, in particular esterases, in contrast to cancer cells. Thus in this implementation, only cancer cells will be labelled with antibodies coupled to the labelled isotope; the action of the esterases in the healthy cells will lead to a leaching of the isotope into the general circulation, and thus only cancer cells will benefit from specific and differential labelling.

The present invention also concerns a process for determining or localising the possible presence in an individual of a tumour or of cancerous cells in which the product of a gene from the myc family is overexpressed, comprising an in vitro, ex vivo or in vivo labelling of said cells or said tumour with an anti-ferritin monoclonal antibody or a fragment thereof coupled directly or indirectly to a substance emitting a signal, said antibody or said fragment recognising an epitope common to acidic and basic human ferritins. In this process, the antibody is preferably coupled to a radioactive isotope; by way of example, indium 111 is particularly suitable when using the monoclonal antibodies of the invention in immunoscintigraphy. The quality of the monoclonal antibodies of the invention as described above, namely its specificity and affinity, is important in the determination or localisation process of the invention.

The skilled person will know how to couple the mono- or bi-specific antibody to the suitable signal and how to detect the signal and/or localise a tumour or tumour cells. Examples that can be cited are fluorescence emitters or luminescence emitters coupled to the antibody by any suitable method. One example of a method that is widely used is avidin/biotin coupling.

The invention also provides the product of coupling between a monoclonal antibody as described above and with characteristics of specificity towards human H and L ferritins and an affinity of more than $10^{-9}$ mole/litre, and a substance X selected from the group formed by:

beta-, gamma- or alpha-emitting radioisotopes;
cytotoxic A chain ricin or abrin molecules or A chain diphtheria toxin;
cytolytic substances of the methotrexate, mitomycin, taxol or adriamycin type;
antisense RNA and DNA.

It also concerns coupling products in which X is stabilised by a liposome or cationic emulsion type vector. It also concerns a coupling product in which a spacer constituted by a carboxylic 5 and 15 carbon atom chain is integrated into the coupling product and can liberate the X molecule when the coupling product is brought into the presence of endogenous esterases.

Within the different aspects of the invention described above, it is particularly surprising to observe that the use of isoferritins monoclonal antibodies or fragments thereof, if appropriate coupled to a radioactive isotope or to a cytotoxic or cytostatic substance has an application in diagnosis and the treatment of all of the tumours and cancer cells which overexpresses the myc gene products. Without in any way limiting the field of application, different types of cancers for which this type of treatment would appear to be particularly suitable are:

a. Hodgkin's disease:

It is already known that patients that are refractory to conventional treatments for the disease have been able to be treated with an antiferritin polyclonal antibody labelled with yttrium 90 (H. M. Vriesendorp et al., (1997), Cancer Supplement, December 15, vol. 80, n° 12, pages 27–21).

b. Cancer of the pancreas:

There are 8000 new cases per year of cancer of the pancreas in France. This cancer has a catastrophic prognosis in that less than 3% survive to five years. This cancer is very chemo-insensitive; it is radio-sensitive but radio incurable (critical organ). Current treatments are surgery, if possible, radiotherapy and per-operative radiotherapy. The advantage of using antiferritin monoclonal antibodies coupled to a radioactive isotope, in particular yttrium 90, is that the deliverable dose of radiotherapy is potentially multiplied by 20, accompanied by a secondary toxicity that is very low. The consequence of targeting prevents destruction of the radioactive isotope in the general circulation; the isotope is targeted directly at the tumours.

c. Hepatocellular carcinoma:

This liver cancer represents about 15 cases per 100000 inhabitants. It is operable in 20% of cases with a prognosis of 40% at five years. For the 80% of inoperable cases, the prognosis is 10% at 5 years No treatment has yet proved effective apart from radioactive lipiodol. Treatment using the compounds of the invention can increase the therapeutic index (residence time/discharge time) from 4 to 10 with respect to treatment with iodine-131 labelled lipiodol, also because the isotope is administered directly to the tumour.

d. Carcinoma of the head and neck (upper aerodigestive tract cancers)

These cancers affect 12000 patients per year in France and have a 40% survival rate at 5 years; 15% of the survivors have a high risk of metastatis.

All of the cancers cited above produce ferritin. Further, while ferritin is expressed only intracellularly in healthy cells, in the neoplastic process, usually associated with the c-myc oncogene, ferritin is generally expressed on the cell membrane. It thus appears clear that providing a coupling product between monoclonal antibodies and an antiferritin molecule X such as that defined above can specifically target a wide variety of tumours or tumour cells, which all hyper-express a gene from the myc family. In the case of a treatment with metabolic radiotherapy, the use of an IgM is advantageous because of its slow diffusion and longer lifetime.

The above list of tumoral diseases is not exhaustive. Neuroblastomas, lung or ovarian cancers also exhibit an overexpression of c-myc.

The accompanying figures illustrate the invention and its performance without in any way limiting it.

EXAMPLE 1

Producing Antiferritin Monoclonal Antibodies
a) As stated above, it is important that the antigen used to immunise the cells is obtained in a high degree of purity. The original technique used is described in table II below.

TABLE II

| Standardisation and immunisation of mice | |
|---|---|
| Human Minkowsky-Chauffard spleen | Slice and grind |
| | Sonicate 20 min (setting C, constant/G40) |
| Sonicated spleen | Heat to 70–75° C. for 10 min |
| Ferritin-enriched spleen extract | Centrifuge 25000 g for 10 min |
| Centrifuge supernatant | +acetic acid − pH 4.8 |
| | contact 2 hours at 4° C. |
| | +K2HPO4 = pH 6.5 |
| Centrifuge supernatant | Fractional precipitation |
| | 50% ammonium sulphate |
| | overnight, 4° C. |
| | centrifuge 2500 g for 10 min |
| Centrifuge residue | Take up in 100 mM K2HPO4 buffer, pH 7.2 |
| | Dialysis in 100 mM K2HPO4 buffer, pH 7.2 |
| | Overnight, 4° C. |
| Dialysis supernatant | Re-precipitation from 5% cadmium sulphate |
| | Overnight at 4° C. |
| | Centrifuge at 10000 g for 30 min |
| Centrifuge residue | Take up in 100 mM K2HPO4 buffer, pH 7.2 |
| | Dialysis in 100 mM K2HPO4 buffer, pH 7.2 |
| | Overnight, 4° C. |
| Dialysis supernatant | Chromatography on SUPERDEX 200 |
| | Concentration by AMICON ultrafiltering |
| | 100 mM phosphate buffer, pH 7.2 |
| Ferritin 50 with cadmium sulphate | Physico-chemical and immunochemical analyses (QC) |

An analysis of the chromatogram after chromatography on SUPERDEX 200 is shown in FIG. 2.
b) Mouse immunisation:
The production and cloning of monoclonal antibodies by mouse immunisation was carried out using the conventional Köhler and Milstein method.
c) Production and purification of monoclonal antibodies produced by hybridomas:
The hybridomas were grown in an in vitro cell culture system on multitrays (Nunc, reference 16795).
The cells were cultured in RPMI 4+TCH. The innoculum was constituted by $5 \times 10^7$ in 200 ml of TCH. RPMI medium (about 100 to 200 ml) was added every other day until confluence. The supernatant was harvested after about a week when the cells had died.

The supernatant was concentrated ten times then loaded onto a chromatography column carrying protein G sepharose FF (Pharmacia), after diluting by half in 20 mM sodium phosphate buffer, pH 7. After chromatographing, the antibody was eluted with a 0.1 M HCl glycine buffer, H 7, and the column was immediately desalted against 0.2 M potassium phosphate buffer, pH 7.2. The purity obtained was at least 95%. The isotype, the isoelectric point and the reactivity by immunodiffusion were then studied using these purified preparations.

Of the different antibodies obtained and shown in Table I above, monoclonal antibodies B8 and M29 appear to be of the greatest interest in terms of affinity and specificity for human cells. These two antibodies are of isotype IgG 1 Kapa.

Histochemical results:
Histochemistry experiments were carried out with a B8 monoclonal antibody coupled to peroxidase.
a) on Hodgkins ganglion;
b) on pancreatic adeno-carcinoma. An immunohistochemical study was carried out with AMB 8LK antibody diluted to $1/250^{th}$ in PBS buffer using the conventional alkaline phosphatase technique.

The tissues were fixed in a bath of 4% paraformaldehyde, 0.1 M ethenolamide pH 7.4 and cast into paraffin. 5µ sections were cut. After dewaxing in xylenethanol baths, the non specific reactions were blocked by incubating the preparation with foetal calf serum. The section was incubated with AMB 8LK antibodies in a $1/25^{th}$ dilution for one hour at ambient temperature. The fixed AMB 8LK was revealed with a peroxidase system (Cordell J-L et al., J. Histochem 1984 32: 219–229).

The results obtained are shown in FIG. 1.
Observation of photographs A and B indicate that all of the Reed Stomberg tumour cells are positive for ferritin expression.

Observation of photograph C also shows that the tumour itself is highly positive for ferritin expression.

EXAMPLE 2

Results of Sandwich ELISA Test
Recognition of repetitive epitopes that are common to acidic and basic human isoferritins can improve the diagnostic and therapeutic properties of antibodies.

The sandwich ELISA test can identify antibodies directed against repetitive epitopes. The principle of the test resides in fixing the same antigen firstly with a first antibody fixed on the solid phase and secondly with a second free antibody carrying a label (for example enzymatic). For the test to function, at least two antibodies must recognise the same molecule; in other words, the recognised molecule comprises at least two repeated epitopes.

The monoclonal antibody of the invention AMB 8LK was used to carry out a sandwich ELISA test to detect human ferritins.

More precisely, the ELISA test was carried out using the following protocol:
a) incubation:
50 µl of a standard or of patient's serum was deposited in each well. 200 µl of AMB 8LK antiferritin antibody conjugated with peroxidase was added. Beads coated with AMB 8LK antibody were then added to each well. The mixture was incubated for two hours with stirring at ambient temperature. It was then washed three times with a solution of 1.5 ml of 9% NaCl and 2% Tween 20.

b) Colour reaction:

300 µl of substrate (OPD) was deposited in each tube. The mixture was incubated for 30 minutes at ambient temperature in the absence of light. 2 ml of 1M HCl was added to each tube.

c) Reading:

The absorbance was measured at 492 nm, reflecting the quantity of antibody fixed to the ferritin, itself fixed to the antibody on the solid phase.

FIG. 3 shows the results of the test.

It could detect human ferritin of the following origins:

spleen;
liver;
heart
placenta.

The results shown here show that it is possible to carry out a sandwich test with AMB 8LK antibody. These results demonstrate that the antibody recognises a common repetitive epitope on human isoferritins.

The invention claimed is:

1. A method for in vivo targeting a molecule X to tumours or tumour cells which exhibit an overexpression of the product of a gene from the myc family, in a human having said tumour or tumour cells, said method comprising:
   a. providing an antiferritin monoclonal antibody or a fragment thereof, said antibody or said fragment recognizing an epitope that is common to acidic and basic human ferritins, and has an affinity of more than $10^{-9}$ mole/liter;
   b. coupling said antibody or fragment thereof to said molecule X to provide a coupling product; and,
   c. administering said coupling product to a human in vivo; wherein said, antiferritin monoclonal antibody or fragment thereof targets molecule X to said tumour or tumour cells which exhibit an overexpression of the product of a gene from the myc family via binding of said monoclonal antibody or fragment thereof to said tumour or tumour cells.

2. The method of claim 1, wherein said epitope that is common to acidic and basic human ferritins is repetitive.

3. The method of claim 1, wherein said antiferritin monoclonal antibody is an IgG.

4. The method of claim 1, wherein the monoclonal antibody is an IgM or a fragment thereof.

5. The method of claim 1, wherein X is a beta-emitting radioisotope.

6. The method of claim 1, wherein X is a toxic molecule.

7. The method of claim 6, wherein said toxic molecule X is selected among the group of the A chain ricin or abrin type, A chain diphteria toxin and a cytolytic substance of the methotrexate, mitomycin, taxol or adriamycin type.

8. The method of claim 1, wherein X is a cytostatic and/or cytotoxic antisense RNA.

9. The method of claim 1, wherein X is a substance stabilized by a liposome type vector.

10. The method of claim 1, wherein X is an antibody recognizing a specific receptor of a tumour cell.

11. The method of claim 1, wherein X is an antibody recognizing an antigen of lymphoid, dendritic, macrophagic or natural killer type cells.

12. The method of claim 1, wherein X is an alpha-emitting radioisotope.

13. The method of claim 1, wherein X is a gamma-emitting radioisotope.

14. The method of claim 1, wherein a C5 to C15 spacer is integrated into the coupling product and can liberate the X molecule when the coupling product is brought into the presence of esterase.

15. A method to determine or localize in an individual the presence of a tumour or cancerous cells in which the product of gene from the myc family is overexpressed, comprising:
   a. providing an antiferritin monoclonal antibody or a fragment thereof, said antibody or said fragment recognizing an epitope that is common to acidic and basic human ferritins, and has an affinity of more than $10^{-9}$ mole/liter;
   b. coupling directly or indirectly said antibody or fragment thereof to a signal emitting substance to provide a coupling product;
   c. administering said coupling product to an individual in vivo; and,
   d. localizing tumour or cancerous cells by detecting the signal emitted by said coupling product.

16. The method of claim 15, wherein said epitope common to acidic and basic human ferritins is repetitive.

17. The method of claim 15, wherein said antibody or fragment thereof is coupled to a beta-emitting yttrium-90 type.

18. The method of claim 15, wherein the antibody is coupled to a substance emitting a fluorescent or luminescent signal.

19. The method of claim 15, wherein the antiferritin monoclonal antibody is an IgG.

* * * * *